US008775360B2

(12) United States Patent
Nakamura (10) Patent No.: US 8,775,360 B2
(45) Date of Patent: Jul. 8, 2014

(54) SIGNIFICANCE EVALUATION PROGRAM AND RECORDING MEDIUM

(76) Inventor: Masao Nakamura, Seki (JP)

(*) Notice: Subject to any disclaimer, the term of this patent is extended or adjusted under 35 U.S.C. 154(b) by 328 days.

(21) Appl. No.: 12/772,584

(22) Filed: May 3, 2010

(65) Prior Publication Data

US 2011/0066584 A1  Mar. 17, 2011

(30) Foreign Application Priority Data

Sep. 15, 2009 (JP) ................................ 2009-213667

(51) Int. Cl.
*G06N 5/02* (2006.01)
*G06F 17/18* (2006.01)
*G06F 9/44* (2006.01)

(52) U.S. Cl.
CPC . *G06N 5/02* (2013.01); *G06F 17/18* (2013.01)
USPC .......................................................... 706/52

(58) Field of Classification Search
CPC .................................. G06N 5/02; G06F 17/18
See application file for complete search history.

(56) References Cited

U.S. PATENT DOCUMENTS

| 7,801,591 | B1* | 9/2010 | Shusterman | 600/509 |
| 2004/0241730 | A1* | 12/2004 | Yakhini et al. | 435/6 |
| 2007/0239361 | A1* | 10/2007 | Hathaway | 702/19 |
| 2009/0281896 | A1* | 11/2009 | Brooks | 705/14.44 |

FOREIGN PATENT DOCUMENTS

JP  2000-266710 A  9/2000

OTHER PUBLICATIONS

Karp, Andrew. Steps to Success with SAS® Output Delivery System, Mar. 2008, SAS Global Forum.*
Karp, Andrew. Getting Un-Stuck in the Traffic Lighting, 2006.*
Xue, Using SAS to Analyze the Summary Data, 2006.*
Kelly et al, KGraph: a system for visualizing and evaluating complex genetic associations, 2007.*
Romualdi et al, IDEG6: a web tool for detection of differentially expressed genes in multiple tag sampling experiments, 2002.*
Speer et al, Opposite Effects of High and Low Frequency rTMS on Regional Brain Activity in Depressed Patients, 2000.*
"Effect of Taking a Bath Before Bedtime on Nocturnal Sleep in Women With Cold Constitutions", released by the Tsumura Lifescience Co., Ltd., Online, Jul. 3, 2008, News Release, 2008, searched on Internet on Aug. 26, 2009, <http://www.tsumura-ls.co.jp/news/2008/0703_rel.htm> English translation of the bar graphs in p. 3, attached.

(Continued)

*Primary Examiner* — Jeffrey A Gaffin
*Assistant Examiner* — Mikayla Chubb
(74) *Attorney, Agent, or Firm* — Westerman, Hattori, Daniels & Adrian, LLP (57) ABSTRACT

The program makes a computer function as a significance evaluation unit including a statistical equation storage unit which stores algorithms of a plurality of statistical methods, a significance probability calculation unit which calculates significance probability for each of the evaluation items with the algorithm read out from the statistical equation database based on an input signal indicating one statistical method selected, a significance determination unit which determines a magnitude relationship between the significance probability and a significance level which is previously set or input and gives significance information to each of the evaluation items, and an evaluation result output unit which makes a display device output a matrix table in which the same number of cells as that of the evaluation items are provided such that each cell is corresponded to each evaluation item and cells of n columns or n rows are arranged.

3 Claims, 9 Drawing Sheets

(56) References Cited

OTHER PUBLICATIONS

T. Tominaga et al, "Epidemiologic Study for Occupational Low Back Pain and Quality of Life in Labourers", Japanese Society of Occupational Medicine and Traumatology, 2003, pp. 423-427, vol. 51, No. 6. English abstract is originally included in the document. English translation of Table 3, is attached.

Japanese Office Action dated Jun. 4, 2013, issued in corresponding Japanese Patent Application No. 2009-213667 (2 pages).

Sueda et al., "Abnormal Process Retrieval System", Toshiba Technological Publication vol. 19-37, pp. 141-144, Jul. 16, 2001, Japan with partial translation and cited in Japanese Office Action dated Jun. 4, 2013.

Sannomiya et al., "Subject Assesment of Voice Entry and Keyboard Entry", Workshop of Acoustical Society of Japan, pp. 109-110, 1987, Japan with partial translation and cited in Japanese Office Action dated Jun. 4, 2013.

\* cited by examiner

FOR PATIENTS

YEAR / MONTH / DATE

NAME : _____________

When your back or legs hurt, you may find it difficult to do some of the things you normally do. This list contains sentences that people have used to describe themselves when they have back or leg pain. As you read the list, think of yourself today. When you read a sentence that describes you today, put a circle against it. If the sentence does not describe you, then leave the space blank and go on to the next one.

| | | |
|---|---|---|
| 1. | I stay at home most of the time because of pain. | |
| 2. | I change position frequently to try and get my back or legs comfortable. | |
| 3. | I walk more slowly than usual because of pain. | |
| 4. | Because of pain, I am not doing any of the jobs that I usually do around the house. | |
| 5. | Because of pain, I use a handrail to get upstairs. | |
| 6. | Because of pain, I lie down to rest more often. | |
| 7. | Because of pain, I have to hold on to something to get out of an easy chair. | |
| 8. | Because of pain, I try to get other people to do things for me. | |
| 9. | I get dressed more slowly then usual because of pain. | |
| 10. | I only stand for short periods of time because of pain. | |
| 11. | Because of pain, I try not to bend or kneel down. | |
| 12. | I find it difficult to get out of a chair because of pain. | |
| 13. | My back is painful almost all the time. | |
| 14. | I find it difficult to turn over in bed because of pain. | |
| 15. | My appetite is not very good because of pain. | |
| 16. | I have trouble putting on my socks (or stockings) because of pain. | |
| 17. | I only walk short distances because of pain. | |
| 18. | I sleep on my back less well because of pain. | |
| 19. | Because of pain, I get dressed with help from someone else. | |
| 20. | I sit down for most of the day because of pain. | |
| 21. | I avoid heavy jobs around the house because of pain. | |
| 22. | Because of pain, I am more irritable and bad tempered with people than usual. | |
| 23. | Because of pain, I go upstairs more slowly than usual. | |
| 24. | I stay in bed most of the time because of pain. | |

GIFU UNIV. *Department of Orthopaedic Surgery, Gifu University, School of Medicine*

| OCCUPATION | PHARMACEUTICAL COMPANY | CARE WORK | P VALUE |
|---|---|---|---|
| LOW BACK PAIN EXPERIENCE | 68% | 82% | < 0.005 |
| ″   VAS | 28.8 | 38.7 | < 0.002 |
| LOW BACK PAIN NOW | 31% | 62% | < 0.0001 |
| ″   VAS | 6.9 | 23.5 | < 0.0001 |
| SEX | MALE 85.5% | FEMALE 83.5% | < 0.0001 |
| AGE | 42.4 YEARS OLD | 38.9 YEARS OLD | < 0.01 |
| WORKING STYLE | DAY SHIFT 92% | IRREGULAR 47% | < 0.0001 |
| WORKING POSITION SITTING POSITION | 40% | 11.6% | < 0.0001 |
| STANDING POSITION | 18.5% | 9.1% | < 0.0001 |
| CARRYING POSITION | 10.5% | 54.3% | < 0.0001 |
| TWISTING POSITION BENDING OVER POSITION | 0% | 29.9% | --- |
| OTHERS | 30.4% | 10.4% | < 0.0001 |
| LEAVE PERIOD | 4.2 DAYS | 5.1 DAYS | NS |

SIGNIFICANCE EVALUATION PROGRAM AND RECORDING MEDIUM

The present application is based on Japanese Priority Application No. 2009-213667 filed on Sep. 15, 2009 with the Japan Patent Office, the entire contents of which are hereby incorporated by reference.

BACKGROUND OF THE INVENTION

1. Field of the Invention

The present invention relates to a program for statistically evaluating significance of data obtained from specimens. In particular, the invention relates to a significance evaluation program suitable to a case where there are a plurality of evaluation items and a recording medium in which the significance evaluation program is stored and which can be read out by a computer.

2. Description of Related Art

It is difficult to investigate for all in a population whether a certain treatment offered relates to obtained data in terms of a certain evaluation item, or whether a certain condition satisfied relates to obtained data in terms of a certain evaluation item in a case where the effect of dug administration is needed to be checked or the like. Therefore, as the drug administration is exemplified, a specimen to which a drug is administered and a specimen to which a placebo is administered are extracted from each population. Then, it is checked whether there is any difference between data obtained from both specimens in terms of the evaluation item. If there is a difference between the data, a comparison test for significantly examining whether the difference is significant is performed. That is to say, the comparison test is performed for significantly examining whether the difference between the specimens can be based on difference between the populations.

In order to significantly examine whether the difference is significant, a hypothesis (null hypothesis) that administration of the drug is not related to obtained data in terms of the evaluation item in the population is made. Then, a statistical probability, that is, a significance probability that a specimen providing the practically obtained data in terms of the evaluation item is extracted from the population in accordance with the hypothesis is calculated. Note that the significance probability is referred to as "p value" in some cases below. Then, the calculated p value is compared with a predefined significance level. If the significance probability is smaller than the significance level, the null hypothesis is rejected. This results in that the difference between the data observed in terms of the evaluation item as for the administration of the drug is determined to be significant at the defined level. As the significance level, although 0.05 (5%) or 0.01 (1%) is generally used in many cases, 0.03 or 0.1 is used in some cases depending on disciplinary fields, subjects to be investigated, or the like The result of the significance evaluation performed in such a manner is conventionally indicated with the following ways in general. That is, the result of the significance evaluation is indicated with a table in which p values are listed for evaluation items, or with a graph in which data obtained for the specimens is indicated with a bar graph or a line graph and p values are written into the graph (for example, see Toshikatsu TOMINAGA and two others, "EPIDEMIOLOGIC STUDY FOR OCCUPATIONAL LOW BACK PAIN AND QUALITY OF LIFE IN LABORERS", published by Japanese society of occupational medicine and traumatology, 2003, vol. 51, No. 6, pp. 423-427 and Tsumura Lifescience Co., Ltd. "EFFECT OF TAKING BATH BEFORE BEDTIME ON NOCTURNAL SLEEP IN WOMEN WITH COLD CONSTITUTIONS", released by Tsumura Lifescience Co., Ltd., Online, Jul. 3, 2008, News Release, 2008, searched on Internet on Aug. 26, 2009, <URL: http://www.tsumura-ls.co.jp/news/2008/0703_rel.htm>.

Figure 7:
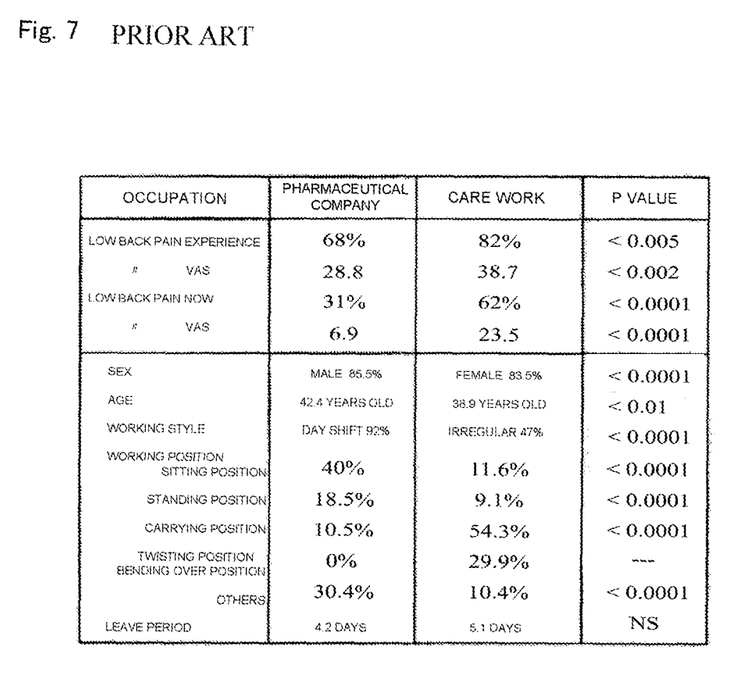
FIG. 7 is an example of conventional indications indicating results obtained by the comparison test with a table in which p values are listed for evaluation items.

In Toshikatsu TOMINAGA and two others, "EPIDEMIOLOGIC STUDY FOR OCCUPATIONAL LOW BACK PAIN AND QUALITY OF LIFE IN LABORERS", published by Japanese society of occupational medicine and traumatology, 2003, vol. 51, No. 6, pp. 423-427, an association between occupation or lifestyle and low back pain is examined. In a table quoted in FIG. 7, people who work in a pharmaceutical company and care workers are set to be subjects to be compared. Then, a comparison test is performed on the subjects in terms of evaluation items such as presence/absence of low back pain and working positions during work and the p value is listed for each evaluation item.

Figure 8A:
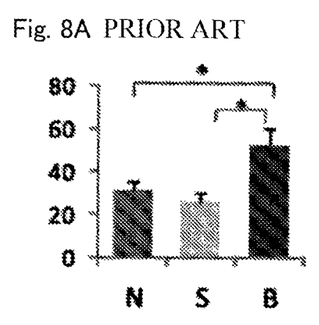
FIGS. 8A to 8C are examples of conventional indications indicating results obtained by the comparison test with bar graphs for evaluation items.
Figure 8B:
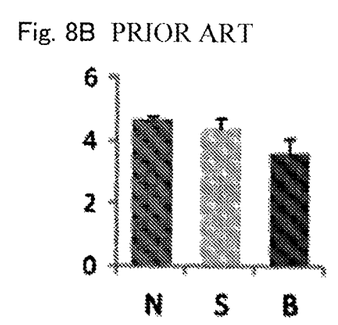
Figure 8C:
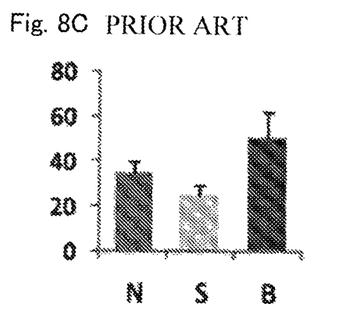

In Tsumura Lifescience Co., Ltd. "EFFECT OF TAKING BATH BEFORE BEDTIME ON NOCTURNAL SLEEP IN WOMEN WITH COLD CONSTITUTIONS", released by Tsumura Lifescience Co., Ltd., Online, Jul. 3, 2008, News Release, 2008, searched on Internet on Aug. 26, 2009, <URL: http://www.tsumura-ls.co.jp/news/2008/0703_rel.htm>, examination of effect on sleep inducement is performed on women with subjective cold constitutions under a condition of not taking a bath (N), taking a shower bath (S) or sitting in a bathtub with bath additive (B). In graphs quoted in FIGS. 8A to 8C, subjective evaluations for a) motivation on awakening, b) drowsiness on awakening and c) feeling of wakefulness on awakening are quantified with Visual Analog Scale (VAS) or the like so as to be indicated with bar graphs. In FIGS. 8A to 8C, asterisks (*) which indicate that p value<0.05 is satisfied are written in the graph for the group where the significance difference is observed. In such a manner, the degree of significance is evaluated in stages. For example, a rule that if p value<0.05 is satisfied, "**" is written into a bar graph or a line graph, and if p value<0.01 is satisfied, "*" is written thereinto is generally adopted.

However, the presence/absence of significance difference or the degree of significance cannot be grasped at a glance from the conventional indications as described above. In particular, if there are a large number of evaluation items, the presence/absence of significance difference or the degree of significance cannot easily understood sensuously and it is extremely difficult to interpret the indicated information. For example, in the indication as in Toshikatsu TOMINAGA and two others, "EPIDEMIOLOGIC STUDY FOR OCCUPATIONAL LOW BACK PAIN AND QUALITY OF LIFE IN LABORERS", published by Japanese society of occupational medicine and traumatology, 2003, vol. 51, No. 6, pp. 423-427, p values are listed for the number of evaluation items so that the listed numerals are not easily understood. Moreover, it is troublesome to compare the p values of the evaluation items with each other when rows of the evaluation items are separated in the indication of Toshikatsu TOMINAGA and two others, "EPIDEMIOLOGIC STUDY FOR OCCUPATIONAL LOW BACK PAIN AND QUALITY OF LIFE IN LABORERS", published by Japanese society of occupational medicine and traumatology, 2003, vol. 51, No. 6, pp. 423-427. On the other hand, in the indication as in Tsumura Lifescience Co., Ltd. "EFFECT OF TAKING BATH BEFORE BEDTIME ON NOCTURNAL SLEEP IN WOMEN WITH COLD CONSTITUTIONS", released by Tsumura Lifescience Co., Ltd., Online, Jul. 3, 2008, News Release, 2008, searched on Internet on Aug. 26, 2009, <URL: http://www.tsumura-ls.co.jp/news/2008/0703_rel.htm>, as many graphs as the evaluation items are required. Therefore, a large amount of time and effort are required to make such graphs. In addition, this imposes a tremendous burden on a reader to examine graphs individually and further study the graphs in a comprehensive manner.

Under these circumstances, there has been a demand of indicating evaluation results of statistical significances so as to be easily grasped at a glance even when there are a large number of evaluation items. Further, a program which is executed so as to calculate p values, evaluate the significances and indicate the evaluation results by controlling hardware has been desired because the statistical processings require a large amount of time and effort if manually operated.

SUMMARY OF THE INVENTION

In view of the above circumstances, an object of the present invention is to provide a significance evaluation program which can indicate evaluation results of statistical significances so as to be easily grasped at a glance even when there are a large number of evaluation items, and calculate p values, evaluate the significances and indicate the evaluation results by controlling hardware, and a recording medium in which the significance evaluation program is stored and which can be read by a computer.

In order to solve the above problem, a significance evaluation program according to an aspect of the invention statistically evaluates significance of difference in data obtained from two specimens in terms of a plurality of evaluation items, and makes a computer function as a significance evaluation unit which includes: a statistical equation storage unit which stores a plurality of statistical methods used for comparison tests as statistical equation database such that the statistical methods are related to algorithms; a significance probability calculation unit which reads out the algorithm from the statistical equation database based on an input signal indicating one statistical method selected and calculates significance probability of the data obtained when it is assumed that there is no significance difference between the two specimens for each of the evaluation items based on the algorithm; a significance determination unit which determines a magnitude relationship between the significance probability and a significance level which is previously set or input and gives significance information indicating the magnitude relationship between the significance probability and the significance level to each of the evaluation items; and an evaluation result output unit which makes a display device output a matrix table in which the same number of cells as that of the evaluation items are provided such that each cell is corresponded to each of the evaluation items, cells of n columns×1 row or 1 columns×n row are arranged when the number of the evaluation items is n, and a significance evaluation indication based on the significance information given to each of the evaluation items is indicated in each of the cells.

The "statistical method" is not particularly limited and any statistical methods can be used as long as the statistical method can be used for a comparison test. For example, as statistical methods used when two specimens which are not corresponded to each other are subjected to a comparison test, the following tests can be used. In a case where data is measurement value, an unpaired t test can be used. In a case where the data is ranking data, a Mann-Whitney U test (Willcoxon rank sum test) can be used. In a case where data is classification data such as presence/absence (1: presence, 0: absence) of data including a case where patients answer a self-completed questionnaire by putting a circle into only cells corresponding to appropriate items in order to evaluate Quality of Life (QOL), a Fisher's exact test and a $\chi^2$ test (chi-squared test) can be used. Further, as statistical methods used when two specimens which are corresponded to each other are subjected to a comparison test, the following tests can be used. In a case where data is measurement value, a paired t test can be used. In a case where the data is ranking data, a Willcoxon signed rank test can be used. In a case where data is classification data, a Signed test can be used.

The "significance level" may be previously set to a predetermined value in the program. Further, the significance level may be set in the following manner. That is, a significance level table composed of a plurality of significance levels is previously stored in the program and the table is displayed on a monitor or the like before the evaluation of the significance is started, then, a user selects a significance level used for the evaluation from the plurality of significance levels. Alternatively, the program may have a configuration where the user is required to input a significant level every time the significance is evaluated. Further, the program may have a configuration where the user can select whether the value set in the program is used or an arbitrary value input by the user is used as the significance level.

Further, the significance level to be compared with the significance probability may be single or plural. For example, when one significant level $\alpha$ is set, presence of significance difference can be indicated by significance information given to evaluation items satisfying p value<$\alpha$, and absence of significance difference can be indicated by significance information given to evaluation items satisfying p value≥$\alpha$. Alternatively, when two significance levels of $\alpha 1$ and $\alpha 2$ ($\alpha 1<\alpha 2$) are set, what the degree of significance is different depending on evaluation items can be indicated by pieces of significance information given to evaluation items satisfying p value<$\alpha 1$, evaluation items satisfying $\alpha 1 \leq$ p value<$\alpha 2$ and evaluation items satisfying p value≥$\alpha 2$.

As the "significance evaluation indication" added to cells based on the significance information indicating a magnitude relationship between the significance probability and the significance level, presence/absence of significance and the degree of significance can be indicated by colored/non-colored marks, difference in colors, concentration density of colors, hatched/non-hatched marks, and difference in hatched patterns, for example. These indications make it possible to make readers easily recognize the presence/absence of significance or the difference in the degree of significance at a glance. Alternatively, symbols such as "⊚", "○", "Δ" and "×" by which the presence/absence of significance or the degree of significance can be recognized sensuously can be indicated.

As the "computer" which is made to function by the program according to the invention as the significance evaluation unit including the statistical equation storage unit, the significance probability calculation unit, the significance determination unit and the evaluation result output unit, a general-purpose computer including a CPU and a main storage device can be used. In the computer, the program according to the invention can be stored in the main storage device.

In the invention having the above configuration, the same number of the evaluation results of the significances as that of the evaluation items can be obtained for one pair of specimens to be compared. At this time, the evaluation result of the significance is determined for each evaluation item by comparing the p value with the significance level. Further, the evaluation results are indicated in one matrix table in which the same number of cells as that of the evaluation items are arranged such that each cell is corresponded to each evaluation item. Then, the significance evaluation indications based on the magnitude relationship between the significance probability and the significance level are indicated in the cells. This makes it possible to make a reader easily grasp the presence/absence of significance or the degree of significance with one table even when there are a large number of evaluation items. Further, the reader is not required to determine the presence/absence of significance or the degree of significance by oneself because the significance evaluation indications as results of determination of the presence/absence of significance or the degree of significance are indicated in the cells of the matrix table. In addition, the evaluation results of the significances can be extremely easily grasped when the significance evaluation indications are indications which are easily identified sensuously by colored/non-colored marks, concentration density of colors, and the like.

If the significance evaluation indication in which nothing is added to cells corresponding to evaluation items indicating no significance observed is set, such evaluation items can be easily identified from evaluation items indicating the significance observed at a glance. Therefore, such significance evaluation indication is preferable. The degree of significance can be easily grasped more sensuously by indicating the color to be deeper as the significance is higher, or indicating the density of hatching to be higher as the degree of significance is higher. Therefore, such significance evaluation indication is also preferable.

In addition, calculation of the p values and evaluation of the significance are performed by controlling the computer with the program, then, the evaluation results as a matrix table are displayed on the display device. Therefore, the statistical processing which originally requires time and labor can be labor saved and made in a short period of time. At the same time, the matrix table which can be easily grasped at a glance as described above can be automatically displayed.

In addition to the above configuration, in the significance evaluation program according to the invention, the significance probability is calculated for each of m comparative subject groups each of which includes two specimens in terms of each of n evaluation items by the significance probability calculation unit and the significance information is given to each of the n evaluation items by the significance determination unit, and the evaluation result output unit makes the display device output the matrix table in which n columns×m rows or m columns×n rows of cells are arranged.

With the above configuration, even when there are a plurality of comparative subject groups as well as the plurality of evaluation items, the entire evaluation results can be indicated in one table without large spaces by indicating the evaluation results as the matrix table of n columns×m rows or m columns×n rows. Further, differences in the significance between a plurality of comparative subject groups can be easily understood in a comprehensive manner by relating to differences in the significance between the plurality of evaluations.

A recording medium according to the invention is a recording medium in which the significance evaluation program as described above is recorded and which can be read by a computer.

The "recording medium" is not particularly limited as long as the recording medium can be read by the computer. For example, a CD-ROM, a flexible disk, a USB flash memory, or the like can be used.

According to the invention having the above configuration, the above excellent program can be executed by using an arbitrary computer by installing the program recorded in the recording medium onto the computer.

Effect of the Invention

As an effect of the invention, a significance evaluation program which can indicate evaluation results of statistical significances so as to be easily grasped at a glance even when there are a large number of evaluation items, and calculate p values, evaluate the significances and indicate the evaluation results by controlling hardware, and a recording medium in which the significance evaluation program is stored and which can be read by a computer are provided.

BRIEF DESCRIPTION OF THE DRAWINGS

FIG. 3 is a questionnaire of the Japanese-version of the Roland-Morris Disability Questionnaire (JRMDQ).

DETAILED DESCRIPTION OF THE EMBODIMENTS

A significance evaluation program (hereinafter, simply referred to as "program") according to an embodiment of the invention will be described with reference to FIG. 1 to FIG. 5 below. It is to be noted that a case where the invention is applied to a program for evaluating effects of drugs administered on patients with a chief complaint of low back pain is described as an example.

The program according to the embodiment is stored in a recording medium which can be read by a computer and is used by installing the program into a computer 1 from the recording medium. The computer 1 includes a central processing unit (CPU), a main storage device and an auxiliary storage device as hardware configurations. The program read from the recording medium is stored in the main storage device so that the CPU performs processings in accordance with the program stored in the main storage device. Further, sample database which will be described later or evaluation results of the significances can be stored in the auxiliary storage device such as a hard disk.

Further, a display device 32 and an input device 31 are connected to the computer 1 to establish a significance evaluation system 9 as a whole. As the display device 32, a monitor 32a, a printer 32b and the like can be exemplified. The monitor 32a can display messages which prompt a user to input information required for evaluating the significance, options relating to information to be input, evaluation results of the significances, and the like. The printer 32b can display evaluation results of the significances and processes of the evaluation. As the input device 31, a keyboard, a pointing device, and the like by which various types of instructions, pieces of information and data are input to the computer 1 can be exemplified.

Figure 1:
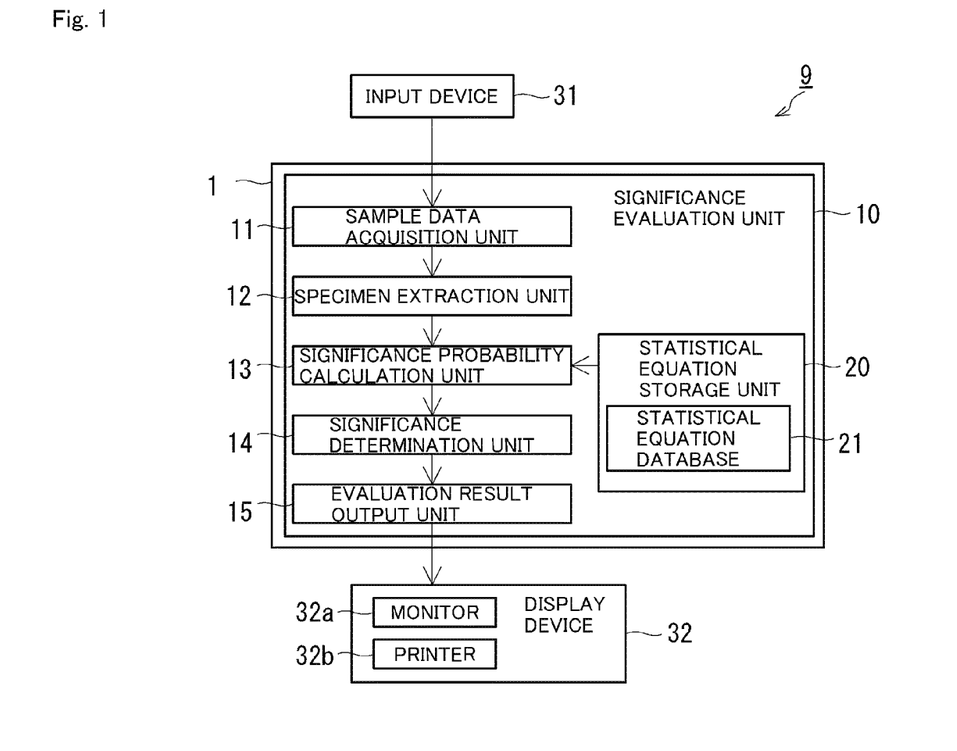
FIG. 1 is a block diagram illustrating a significance evaluation system including, as a main configuration, a computer controlled by a program according to an embodiment of the present invention.

As shown in FIG. 1, the computer 1 includes a significance evaluation unit 10 as a functional configuration by installing the program. The significance evaluation unit 10 further includes a statistical equation storage unit 20, a sample data acquisition unit 11, a specimen extraction unit 12, a significance probability calculation unit 13, a significance determination unit 14 and an evaluation result output unit 15. The statistical equation storage unit 20 stores a plurality of statistical methods used for comparison tests as statistical equation database 21 such that the statistical methods are related to algorithms. The sample data acquisition unit 11 acquires attribute data and evaluation item data for a plurality of samples which are a part of population as sample database related to types of data. The specimen extraction unit 12 extracts samples having data satisfying conditions from the sample database based on input of the conditions that specimens to be compared should satisfy to set comparative subject groups each of which is composed of two specimens. The significance probability calculation unit 13 reads out an algorithm from the statistical equation database based on an input signal indicating one statistical method selected. Then, the significance probability calculation unit 13 calculates a significance probability of data obtained when it is assumed that there is no significance difference between the two specimens for each of evaluation items based on the algorithm. The significance determination unit 14 determines a magnitude relationship between the significance probability and a significance level which is previously set. Further, the significance determination unit 14 gives significance information indicating the magnitude relationship between the significance probability and the significance level to each evaluation item. The evaluation result output unit 15 makes a display device 32 output a matrix table. In the matrix table, the same number of cells as that of the evaluation items are provided such that each cell is corresponded to each of the evaluation items and cells of n columns×1 row or 1 columns×n row are arranged when the number of the evaluation items is n. Further, in the matrix table, a significance evaluation indication based on the significance information given to each of the evaluation items is indicated in each of the cells.

In the embodiment, significance evaluation indications indicated in the cells of the matrix table by the evaluation result output unit 15 indicate the magnitude relationship between the significance probability and the significance level by at least one of colored/non-colored marks, difference in colors, concentration density of colors, hatched/non-hatched marks, and difference in hatched patterns.

Figure 2:
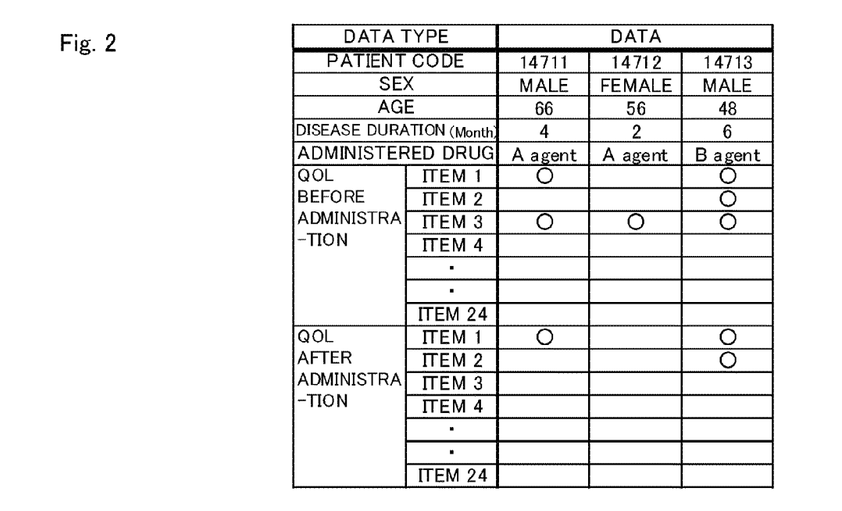
FIG. 2 is an example of sample database.

The sample database may be a database as illustrated in FIG. 2. In the example of FIG. 2, data in items of "sex", "age", "disease duration", and "administered drug" are attribute data used for extraction of specimens and data in items of "QOL before administration" and "QOL after administration" are evaluation item data.

In the embodiment, the Japanese version of the Roland-Morris Disability Questionnaire (JRMDQ) which is one of disease-specific QOL scales and is used for patients with low back pain or lower limb pain is used as the evaluation items. The original version of the JRMDQ was created by Dr. Martin Roland (UK) and Dr. Richard Morris (UK) and the present inventor played central role in translating into Japanese version. Then, the Japanese version of the Roland-Morris Disability Questionnaire (JRMDQ) is spread in Japan. As shown in FIG. 3, the JRMDQ is a self-completed questionnaire including simple questions of 24 items. Patients answer the questions by putting a circle into cells corresponding to any appropriate items. Accordingly, if the number of evaluation items is assumed to be n, n is 24 in the embodiment. For a result of the questionnaire, one point is allocated to one item and 24 points with full marks are given to a case at the lowest level (severe case). In the embodiment, the questionnaires of the JRMDQ are collected before the drug administration is started and after the drug administration for a predetermined period is finished to obtain evaluation item data.

The such sample database which is manually input through the input device 31 can be acquired by the sample data acquisition unit 11. Alternatively, the evaluation item data can be generated to be transmitted to the sample data acquisition unit 11 by displaying questions included in the JRMDQ on a touch panel monitor and making patients touch appropriate items displayed on the monitor with finger, a touch pen, or the like. A configuration in which a sample data acquisition unit 11 can acquire the attribute data from information of medical records which has been converted to digital data can be also adopted. In this case, the attribute data and the evaluation item data can be integrated based on a patient code and a patient name.

Next, a procedure of the significance evaluation with the program according to the embodiment will be described by using detail examples. Here, significance differences in obtained data in terms of the 24 evaluation items of the JRMDQ were evaluated for the following five (five pairs) comparative subject groups 1) to 5) in order to evaluate drug effects of an A agent and a B agent. Each comparative subject group is composed of two specimens.

1) Specimen "before administration of A agent is started" and specimen "before administration of B agent is started".

2) Specimen "before administration of A agent is started" and specimen "after administration of A agent is finished".

3) Specimen "before administration of B agent is started" and specimen "after administration of B agent is finished".

4) Specimen "after administration of A agent is finished" and specimen "after administration of B agent is finished".

5) Specimen "change amount at the time where administration of A agent is finished" and specimen "change amount at the time where administration of B agent is finished".

At first, evaluation of the group 1) is described. A condition of extracting a specimen is specified to be "administered drug=A agent" based on an input from the input device 31 to extract a specimen a including a plurality of samples from the sample database. At the same time, a condition is specified to be "administered drug=B agent" based on an input from the input device 31 to extract the other specimen b including a plurality of samples from the sample database. Then, QOL 24 items before administration for the specimen a and QOL 24 items before administration for the specimen b are set to evaluation items. A list of statistical methods stored as the statistical equation database is displayed on the monitor 32a by the significance probability calculation unit 13 and one statistical method is selected based on the input from the input device 31. At this time, Fisher's exact test is selected as the statistical method because the comparative subject group 1) is composed of two specimens which are not corresponded to each other and data thereof is classification data.

The significance evaluation unit 10 may have a configuration in which a correspondence between the extracted two specimens is determined at the time of extraction of the specimen a and the specimen b, then only applicable statistical equation is extracted from the statistical methods stored as the statistical equation database to display the applicable statistical equation on the monitor 32a.

An algorithm is read out from the statistical equation database based on the selected statistical method. Then, the significance probability (p value) is calculated for each evaluation item by the significance probability calculation unit 13 based on the algorithm. Further, the p value and the significance level are compared with each other by the significance determination unit 14. At this time, as the significance level to be compared with the p value, three significance levels of $\alpha 1=0.01$, $\alpha 2=0.05$ and $\alpha 3=0.1$ are previously set in the embodiment.

Figure 4:
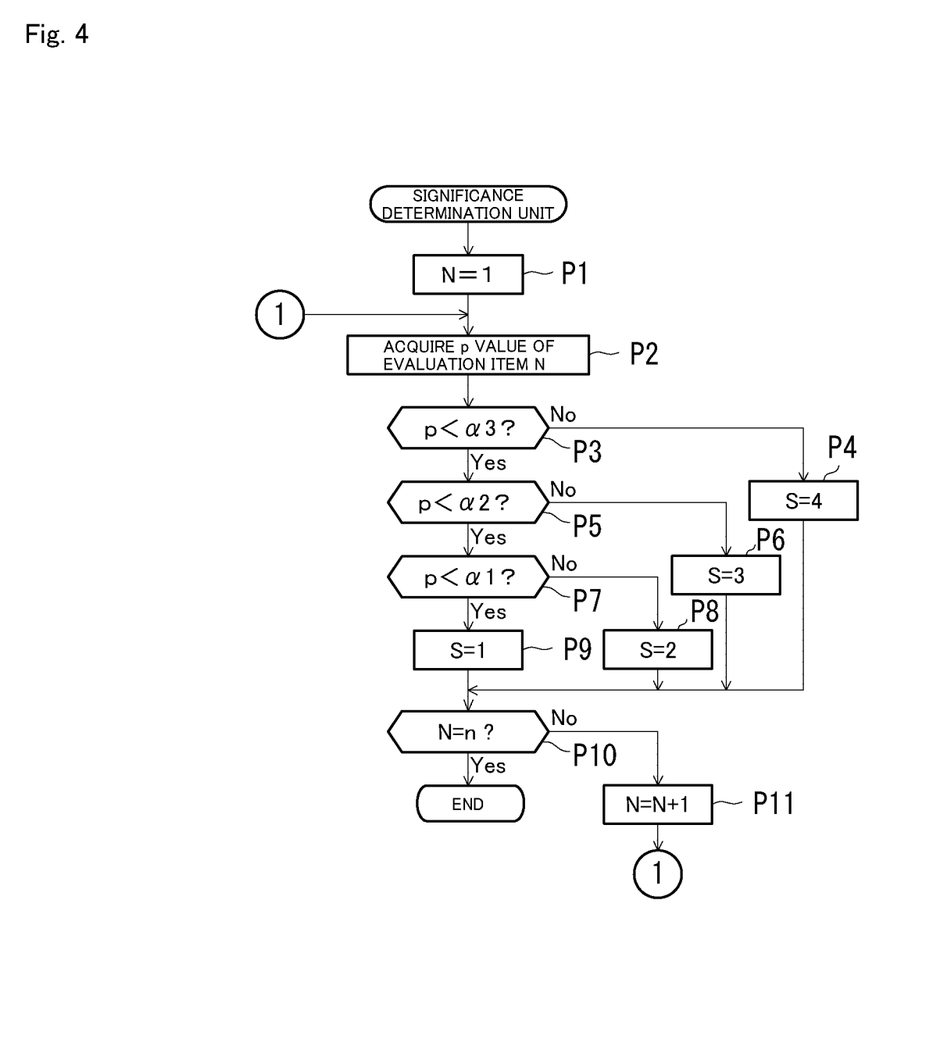
FIG. 4 is a flowchart illustrating a flow of a processing in a significance determination unit.

A flow of a processing by the significance determination unit 14 based on the three significance levels is described with reference to FIG. 4. At first, 1 is set to N indicating what number the evaluation item is listed (item number of the JRMDQ) among n evaluation items (step P1). Then, a p value of the evaluation item N is acquired by the significance probability calculation unit 13 (step P2). Alternatively, the following configuration may be adopted. That is, the evaluation items and the p values are stored once in the auxiliary storage device in a state where the evaluation items are related to the calculated p values for each of the specimen a and the specimen b when the significance probability calculation unit 13 calculates the p values. Then, the significance determination unit 14 reads out the required p value from the auxiliary storage device.

When the p value is acquired, it is determined whether p value<0.1 ($\alpha 3$) is satisfied (step P3). If the p value<0.1 is not satisfied ("NO" in step P3), p value≥0.1 is satisfied and S=4 is given to the evaluation item as significance information indicating a fact that the p value and the significance level have the above relationship (step P4). On the other hand, if the p value<0.1 is satisfied ("Yes" in step P3), it is further determined whether p value<0.05 ($\alpha 2$) is satisfied (step P5). If the p value<0.05 is not satisfied ("NO" in step P5), 0.05≤p value<0.1 is satisfied and S=3 is given to the evaluation item as significance information (step P6). On the other hand, if the p value<0.05 is satisfied ("Yes" in step P5), it is further determined whether p value<0.01 ($\alpha 1$) is satisfied (step P7). If the p value<0.01 is not satisfied ("NO" in step P7), 0.01≤p value<0.05 is satisfied and S=2 is given to the evaluation item as significance information (step P8). On the other hand, if the p value<0.01 is satisfied ("Yes" in step P-7), S=1 is given to the evaluation item as significance information (step P9).

If any one of S=1, 2, 3, 4 is given as significance information at any one step of steps P4, P6, P8 and P9, it is checked whether N reaches to n, that is, whether the significance has been determined on all evaluation items of n=24 (step P10). If N does not reach to n (No at step P10), 1 is added to N and the process returns to step P2. On the other hand, if N reaches to n (Yes at step P10), the process is ended.

The significance information is given to each of all evaluation items by the above processing. Subsequently, the significance evaluation results are displayed on the display device 32 by the evaluation result output unit 15. In the embodiment, a matrix table in which n columns (24 columns) of cells are arranged for each comparative subject group is displayed (matrix indication). At this time, the color monitor 32a and the monochrome printer 32b are used as the display device 32. Here, the significance evaluation indications by colored/non-colored marks and concentration density of colors are displayed on the monitor 32a. On the other hand, the significance evaluation indications by hatched/non-hatched marks and difference in hatched patterns are displayed on the printer 32b.

Specifically, on the monitor 32a, the deepest color is added to cells corresponding to the evaluation items indicating p value<0.01 with the highest significance, that is, the evaluation items to which S=1 is given as significance information. As the degree of significance is lower, the color becomes lighter. That is, the colors added to the evaluation items indicating 0.01≤value<0.05 (significance information S=2) and the evaluation items indicating 0.05≤p value<0.1 (significance information S=3) become lighter in this order. Nothing is added to cells corresponding to the evaluation items indicating p value≥0.1 (significance information S=4) because the significance is not determined to be observed. That is to say, "significance evaluation indication that nothing is added is displayed". On the other hand, on the printer 32b, the highest-density hatching is added to cells corresponding to the evaluation items indicating p value<0.01 with the highest significance (significance information S=1). As the degree of significance is lower, the density of hatching becomes lower. That is, the density of hatchings added to the evaluation items indicating 0.01≤value<0.05 (significance information S=2) and the evaluation items indicating 0.05≤p value<0.1 (significance information S=3) become lower in this order. Nothing is added to cells corresponding to the evaluation items indicating p value≥0.1 (significance information S=4) because the significance is not determined to be observed.

In the example, p value≥0.1 (significance information S=4) is satisfied in all evaluation items for the comparative subject group 1). As shown in the first row of FIG. 5, nothing is added into 24 columns×1 row of cells. Significance evaluation procedures for the comparative subject groups 2) to 5) are substantially the same as that for the comparative subject group 1). However, sign test is selected as a statistical equation for the groups 2) and 3) of which two specimens are corresponded to each other and data is classification data. On the other hand, Fisher's exact test is selected as a statistical equation for the group 4) of which two specimens are not corresponded to each other and data is classification data. Further, Mann-Whitney U test is selected as a statistical equation for the group 5) of which two specimens are not corresponded to each other but data is ranking data which will be described below.

Not actual measured values obtained from answers of the JRMDQ but change amounts between the values before administration of each drug is started and the values after administration thereof is finished are compared for the comparative subject group 5). Therefore, when such comparison test is performed, data before administration and data after administration are compared with each other for each of the sample evaluation items based on the sample database illustrated in FIG. 2. Then, "−1" is given to items indicating improvement by the administration (∘ is marked before administration and nothing is added after administration). "0" is given to items indicating no change (nothing is marked before administration and after administration or ∘ is added before administration and after administration). "1" is given to items indicating aggravation by the administration (nothing is marked before administration and ∘ is marked after administration). A program architecture which makes the computer to function as a unit for adding these data to the sample database is made. With this configuration, data of change amount can be specified as an evaluation item.

Figure 5:
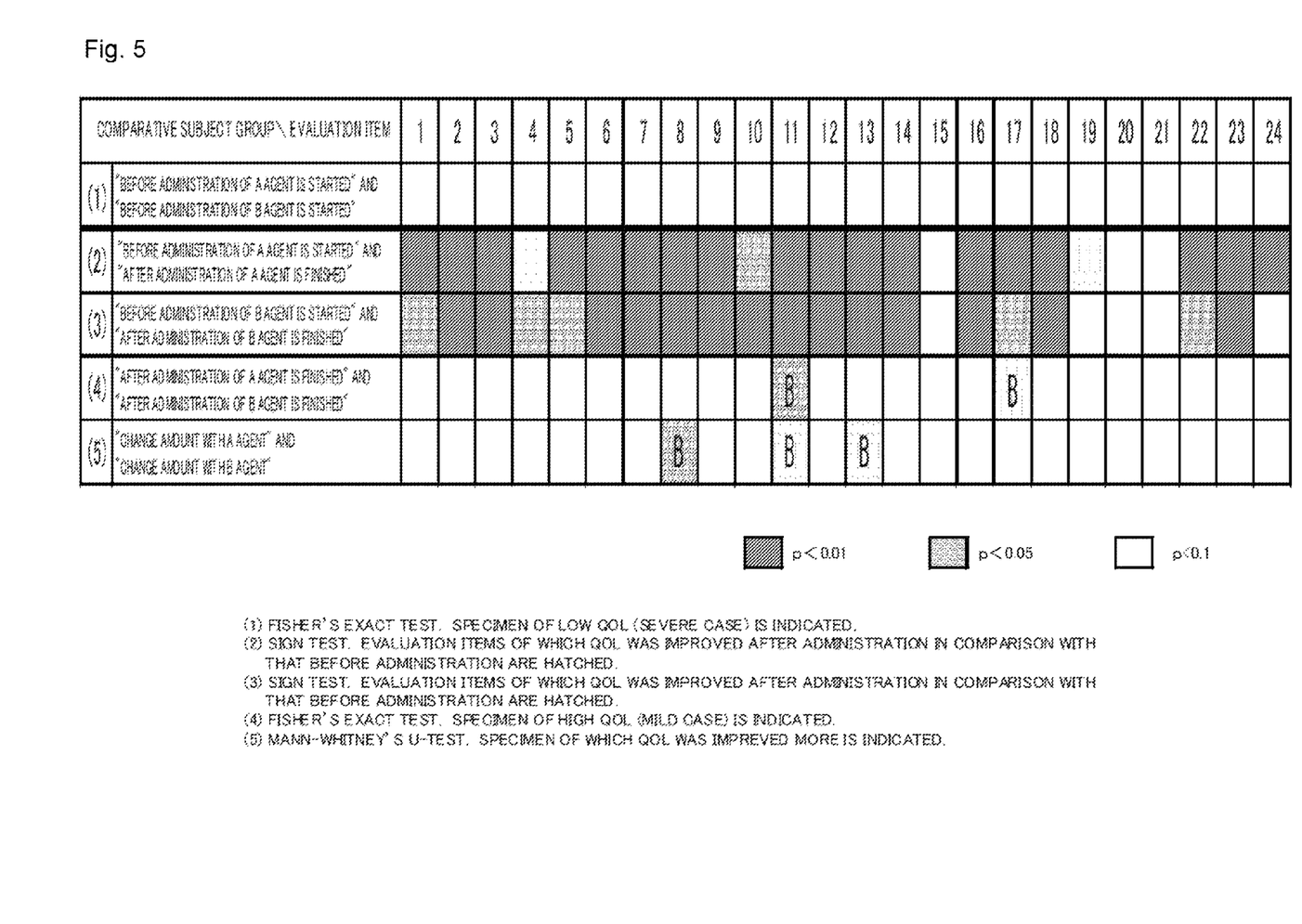
FIG. 5 is an example of a matrix table displayed on a display device by controlling the program according to the embodiment.

If the significance has been evaluated for all the comparative subject groups 1) to 5) as described above, a matrix table in which 24 columns×5 rows of cells are arranged is displayed on the monitor 32a or the printer 32b. FIG. 5 illustrates an example of the matrix table displayed on the monochrome printer 32b in the embodiment. In FIG. 5, the presence/absence and the degree of significance are indicated by the hatched/non-hatched marks and the density of hatchings in the cells.

With such matrix table, the significance of each evaluation item can be grasped at a glance even when a large number of evaluation items n is large as 24. To be more specific, in the comparison 1) between the specimen before administration of the A agent is started and the specimen before administration of the B agent is started, there is no evaluation item indicating the significance difference among 24 items. This means that the specimens are ideal initial states for performing the comparison tests on the comparative subject group 2) to 5).

If the indications in terms of the comparative subject group 2) and 3) are compared, p value<0.05 is satisfied in 19 items for both the A agent and the B agent. This shows improvements in the entire QOL. In addition, although improved items are almost common, there are items of which degree of improvement is higher in one agent than in the other agent. This is an interesting result. For example, the result that the p value<0.01 is satisfied with the A agent and the p value<0.05 is satisfied with the B agent, that is, the result that the degree of improvement with the A agent is higher than that with the B agent is observed in 4 items of $1^{st}$, $5^{th}$, $17^{th}$, $22^{nd}$ items. This shows that improvements in gait and psychological elements are observed with the A agent. On the other hand, the result that the p value<0.01 is satisfied with the B agent and the p value<0.05 is satisfied with the A agent, that is, the result that the degree of improvement with the B agent is higher than that with the A agent is observed in $10^{th}$ item. This shows that an improvement in standing position keeping is observed with the B agent.

Further, with indications in terms of the comparative subject groups 4) and 5), it is obvious that there are items indicating improvement with one of the agents. That is to say, significant improvement tendency at 5% level is observed with the B agent only in $8^{th}$ and $11^{th}$ items. Therefore, it is considered that the B agent is effective for improving psychological elements and positional factors.

Figure 6A:
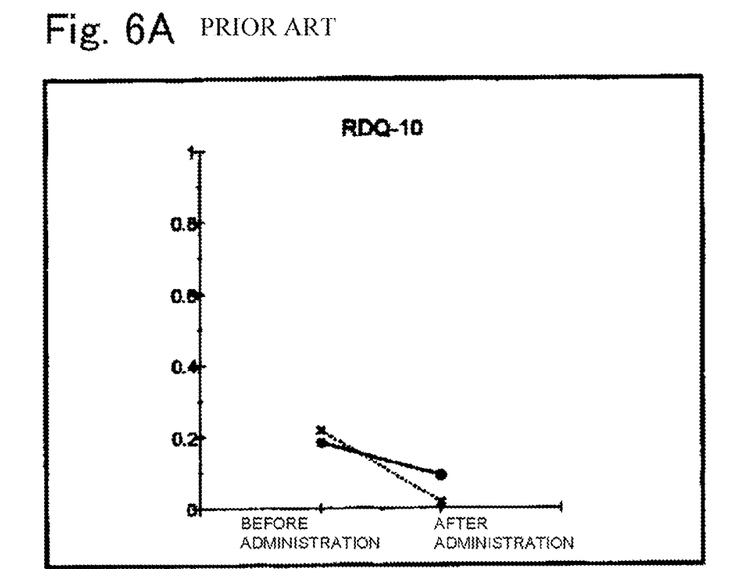
FIGS. 6A to 6F are examples of conventional indications in which significance evaluation results obtained by the same comparison test as in the embodiment are indicated by graphs.
Figure 6B:
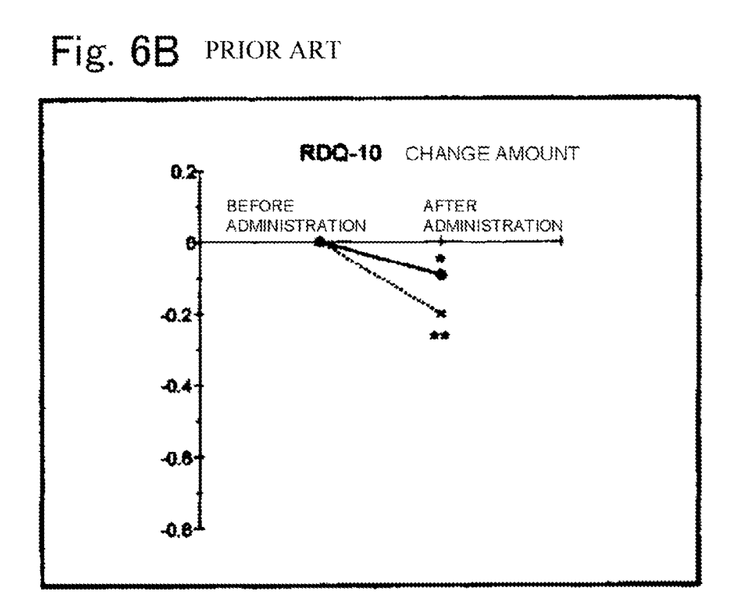
Figure 6C:
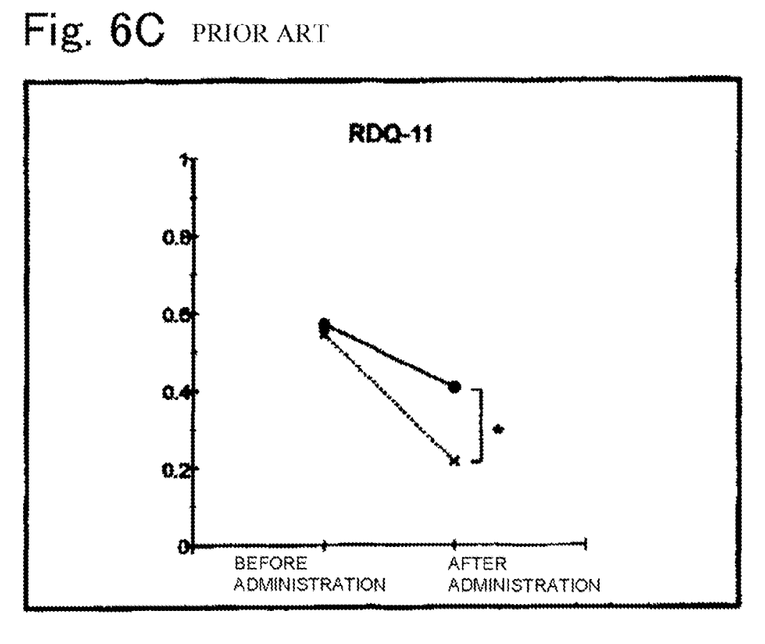
Figure 6D:
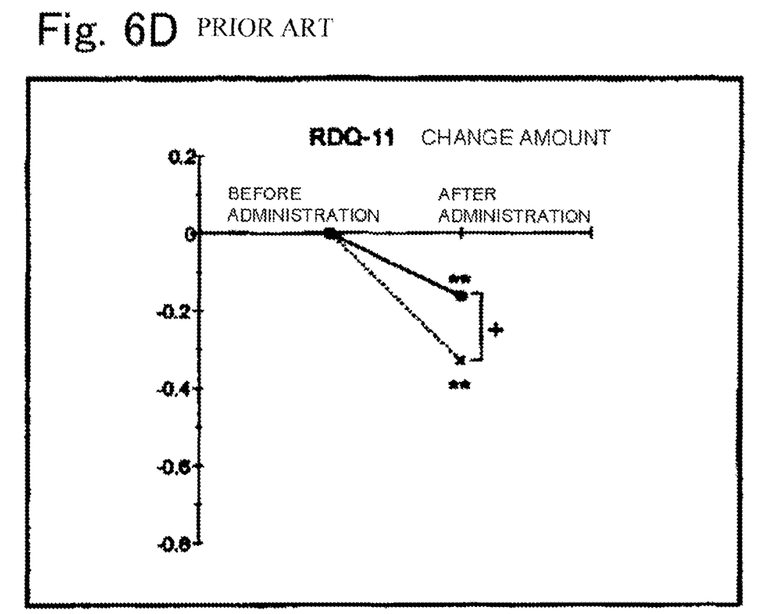
Figure 6E:
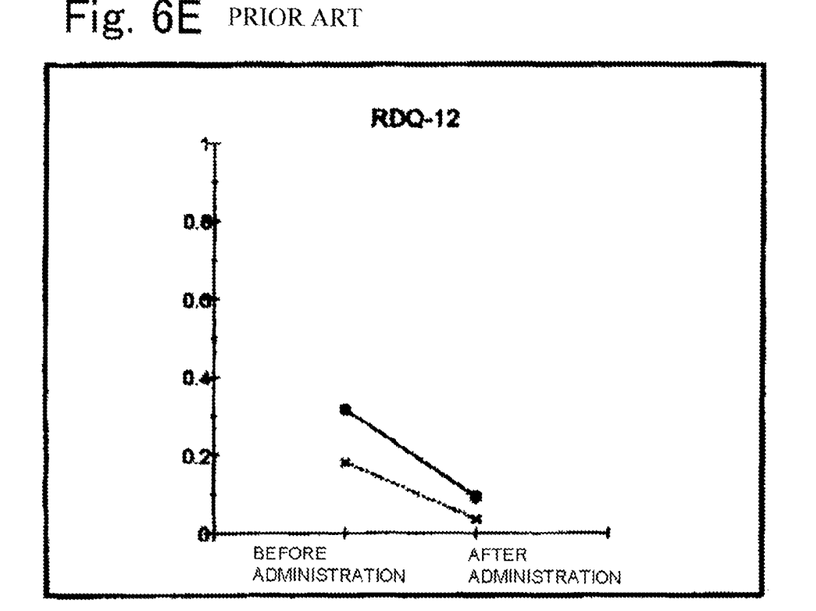
Figure 6F:
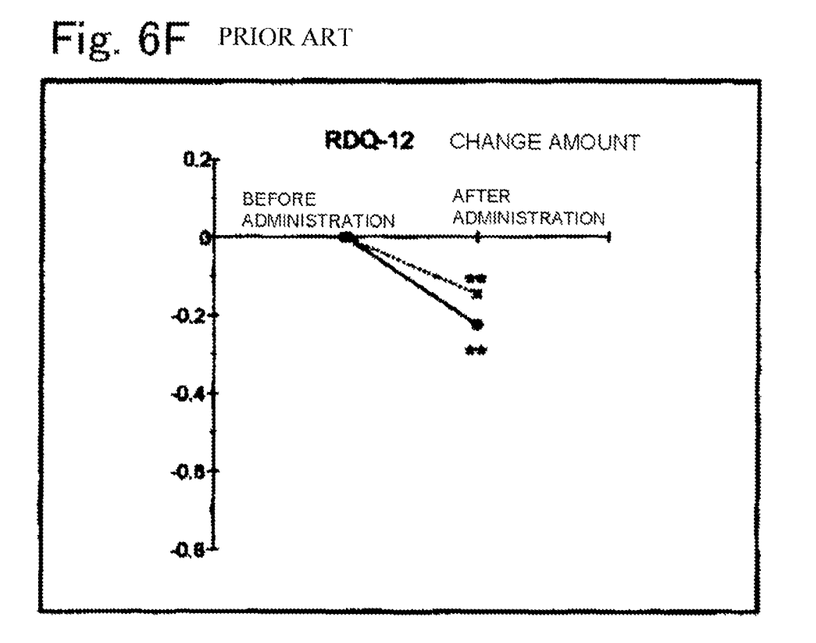

In order to compare the indication with the matrix table according to the embodiment, FIGS. 6A to 6F illustrate a part of results obtained by comparing 24 evaluation items for the same comparative subject groups 1) to 5) as in the above example with line graphs in a conventional way. Here, FIGS. 6A and 6B show the evaluation results obtained by comparing in terms of the evaluation item 10, FIGS. 6C and 6D show the evaluation results obtained by comparing in terms of the evaluation item 11, and FIGS. 6E and 6F show the evaluation results obtained by comparing in terms of the evaluation item 12. FIGS. 6A, 6C and 6E show the evaluation results for the comparative subject groups 1) to 4) in terms of each evaluation item. In FIGS. 6A, 6C and 6E, a longitudinal axis indicates mean value in each specimen when one point is given to each evaluation item. On the other hand, FIGS. 6B, 6D and 6F show the evaluation results for the comparative subject groups 2) to 4) in terms of each evaluation item. In FIGS. 6B, 6D and 6F, a longitudinal axis indicates change amount for the mean values in each specimen when one point is assumed to be given to each evaluation item. Note that the change amount is obtained by subtracting a mean value before administration is started from a mean value after administration is finished. Further, "*" indicates that the p value<0.01 is satisfied, "**" indicates that the p value<0.05 is satisfied, "+" indicates that the p value<0.1 in FIGS. 6A to 6F.

In such conventional indication, 48 of graphs as illustrated in FIGS. 6A to 6F are required to be provided in total in order to indicate results of the comparison tests performed on the comparative subject groups 1) to 5) in terms of 24 evaluation items. A large amount of time and effort are required for examining a large number of 48 graphs one by one and studying the graphs in a comprehensive manner. This imposes a tremendous burden on a reader. In addition, relationships between the significance and the degree thereof cannot be grasped at a glance with the indications of "*", "**", and "+" marked in the graphs.

In contrast, according to the matrix table displayed by the program according to the embodiment, results of the comparison tests performed on a plurality of the comparative subject groups 1) to 5) in terms of each of 24 evaluation items can be indicated in only one table. Further, the entire results such as relationships between the evaluation items can be easily grasped at a glance while the evaluation results for each evaluation item are individually indicated. The degree of significance is indicated by the concentration density of colors or density of hatchings. Note that as the significance is higher, the color becomes deeper and the degree of significance is higher, the density of hatching becomes higher. Accordingly, the degree of significance can be extremely easily understood sensuously.

In addition, extraction of specimens, calculation of significance probability and determination of significance can be performed by the computer 1 by controlling the program according to the embodiment. This makes it possible to perform the statistical processing in an extremely short time rather than a case where the processing is manually operated. Further, the evaluation results are automatically displayed on the display device 32 as a matrix table. Therefore, a table which can be understood at a glance as described above can be output with no effort.

Hereinabove, the invention has been described by the preferred embodiment. However, the invention is not limited to the embodiment and various modifications and changes in design can be made within a range without departing from a scope of the invention as described above.

For example, a case where two specimens to be compared are specimens to which different kinds of two agents are administered and a case where two specimens to be compared are specimens before administration of the agent is started and after administration of the same agent is finished has been described. However, the invention is not limited to the cases. For example, when comparison tests are performed on two specimens of a male patient specimen and a female patient specimen, two specimens of a specimen who is over 65 and a specimen which is under 65, two specimens of a specimen whose disease duration is a predetermined period or longer and a specimen whose disease duration is less than the predetermined period, and two specimens of a specimen to which the drug is administered and a specimen to which the drug is not administered (a placebo is administered), the program according to the invention can be also used.

Further, in the above embodiment, a case where the results of the questionnaire of QOL are set to be evaluation item data is described. However, the invention is not limited thereto. For example, various test values such as blood glucose level, GOT level, GPT level, uric acid level, neutral fat level and cholesterol level are set to be evaluation item data and, the program according to the invention can be used for evaluating significance of these evaluation item data for two specimens different in contents of administration of drug and meals.

Further, a case where the program according to the invention can be used for the comparison test for examining the drug effect has been described hereinbefore. However, the invention can be used for the comparison tests in a wide range of fields. For example, the program according to the invention can be used for the comparison tests for examining whether there is significance difference in degree of satisfaction of consumers between a product manufactured by X company and that manufactured by Y company based on the questionnaire investigation with respect consumers of a certain electronic product. The degree of satisfaction is comprehensively grasped from various viewpoints (a large number of evaluation items) such as usability, diversity of functions, performance, design, price and durability.

What is claimed is:

1. A non-transitory computer-readable storage medium containing a significance evaluation program causing a computer to execute:
    storing in a storage unit a plurality of statistical method algorithms to use for comparison tests as a statistical equation database, the plurality of statistical method algorithms including algorithms used for two specimens that are corresponded to each other and algorithms used for two specimens that are not corresponded to each other;
    extracting two specimens having data satisfying conditions from a sample database based on input of the conditions that the two specimens to be compared should satisfy, the extracting of two specimens being performed for each of m comparative subject groups, with evaluation item data for a plurality of specimens being stored in the sample database;
    determining a correspondence between the extracted two specimens based on the conditions for extraction of the two specimens;
    extracting only the statistical method algorithms from the plurality of statistical method algorithms applicable to the determined correspondence;
    outputting to a display device only the extracted statistical method algorithms;
    reading out one algorithm from the statistical equation database based on an input signal indicating one statistical method selected from the displayed extracted statistical method algorithms;
    calculating a significance probability of the data obtained for each of the m comparative subject groups for each of the n evaluation items, each of which includes two specimens, in terms of n evaluation items, when it is assumed that there is no significance difference between the two specimens for each of the evaluation items based on the algorithm;
    determining a magnitude relationship between the significance probability and a significance level which is previously set or input;
    giving significance information indicating the magnitude relationship between the significance probability and the significance level to each of the evaluation items; and
    outputting to the display device a matrix table of m rows×n columns of cells, each row providing an analysis result for a same combination of the two specimens in the m comparative subject groups for each of the n evaluation items, each row using a different statistical method algorithm, each cell includes only a significance evaluation indication based on the significance information given to each of the evaluation items, and at least one row providing the analysis result of a paired test used for two specimens that are corresponded to each other.

2. A significance evaluation apparatus comprising:
    a statistical equation storage unit which stores a plurality of statistical method algorithms used for comparison tests as a statistical equation database, the plurality of statistical method algorithms including algorithms used for two specimens that are corresponded to each other and algorithms used for two specimens that are not corresponded to each other;
    a computer which extracts two specimens having data satisfying conditions from a sample database based on input of the conditions that the two specimens to be compared should satisfy, the extracting of two specimens being performed for each of m comparative subject groups, with evaluation item data for a plurality of specimens being stored in the sample database, determines a correspondence between the extracted two specimens based on the conditions for extraction of the two specimens, extracts only the statistical method algorithms from the plurality of statistical method algorithms applicable to the determined correspondence, outputs for display only the extracted statistical method algorithms, reads out one algorithm from the statistical equation database based on an input signal indicating one statistical method selected from the displayed extracted statistical method algorithms, and calculates a significance probability of the data obtained for each of the m comparative subject groups, each of which includes two specimens, in terms of each of n evaluation items, when it is assumed that there is no significance difference between the two specimens for each of the evaluation items based on the algorithm, and which determines a magnitude relationship between the significance probability and a significance level which is previously set or input and gives significance information indicating the magnitude relationship between the significance probability and the significance level to each of the evaluation items; and
    a display displaying a matrix table of m rows×n columns of cells, each row providing an analysis result for a same combination of the two specimens in the m comparative subject groups for each of the n evaluation items, each row using a different statistical method algorithm, each cell includes only a significance evaluation indication based on the significance information given to each of the evaluation items, and at least one row providing the analysis result of a paired test used for two specimens that are corresponded to each other.

3. A significance evaluation method comprising the steps of:
    storing in a storage unit a plurality of statistical method algorithms to use for comparison tests as a statistical equation database, the plurality of statistical method algorithms including algorithms used for two specimens that are corresponded to each other and algorithms used for two specimens that are not corresponded to each other;
    a computer extracting two specimens having data satisfying conditions from a sample database based on input of the conditions that the two specimens to be compared should satisfy, the extracting of two specimens being performed for each of m comparative subject groups, with evaluation item data for a plurality of specimens being stored in the sample database;
    the computer determining a correspondence between the extracted two specimens based on the conditions for extraction of the two specimens;
    the computer extracting only the statistical method algorithms from the plurality of statistical method algorithms applicable to the determined correspondence;
    the computer outputting to a display device only the extracted statistical method algorithms;
    the computer reading out one algorithm from the statistical equation database based on an input signal indicating one statistical method selected from the displayed extracted statistical method algorithms;
    the computer calculating a significance probability of the data obtained for each of the m comparative subject groups, each of which includes two specimens, in terms of each of n evaluation items, when it is assumed that there is no significance difference between the two specimens for each of the evaluation items based on the algorithm;

the computer determining a magnitude relationship between the significance probability and a significance level which is previously set or input;

the computer giving significance information indicating the magnitude relationship between the significance probability and the significance level to each of the evaluation items; and the computer outputting to the display device a matrix table of m rows×n columns of cells, each row providing an analysis result for a same combination of the two specimens in the m comparative subject groups for each of the n evaluation items, each row using a different statistical method algorithm, each cell includes only a significance evaluation indication based on the significance information given to each of the evaluation items, and at least one row providing the analysis result of a paired test used for two specimens that are corresponded to each other.

* * * * *